United States Patent
Arlettaz et al.

(10) Patent No.: US 9,241,719 B2
(45) Date of Patent: Jan. 26, 2016

(54) DRIVE SHAFT FOR A SURGICAL REAMER

(75) Inventors: Yvan Arlettaz, Monthey (CH);
Christian Bonjour, Begnins (CH)

(73) Assignee: Chirmat Sarl, Monthey (CH)

(*) Notice: Subject to any disclaimer, the term of this patent is extended or adjusted under 35 U.S.C. 154(b) by 0 days.

(21) Appl. No.: 13/457,159

(22) Filed: Apr. 26, 2012

(65) Prior Publication Data

US 2012/0253348 A1 Oct. 4, 2012

Related U.S. Application Data

(63) Continuation of application No. PCT/EP2010/066120, filed on Oct. 26, 2010.

(30) Foreign Application Priority Data

Oct. 28, 2009 (CH) .................................. 1657/09

(51) Int. Cl.
*A61B 17/56* (2006.01)
*A61B 17/16* (2006.01)
*A61B 17/00* (2006.01)
*A61F 2/30* (2006.01)

(52) U.S. Cl.
CPC ... *A61B 17/1631* (2013.01); *A61B 2017/00831* (2013.01); *A61F 2/30965* (2013.01); *Y10T 408/665* (2015.01)

(58) Field of Classification Search
USPC ..... 408/57, 59, 226, 238, 239 A, 239 R, 127; 606/80
See application file for complete search history.

(56) References Cited

U.S. PATENT DOCUMENTS

| | | | | |
|---|---|---|---|---|
| 4,706,659 A | * | 11/1987 | Matthews et al. | 606/80 |
| 4,751,922 A | * | 6/1988 | DiPietropolo | 606/80 |
| 5,203,595 A | * | 4/1993 | Borzone et al. | 285/325 |
| 5,488,761 A | * | 2/1996 | Leone | 29/2.25 |
| 5,509,919 A | * | 4/1996 | Young | 606/80 |
| 5,645,545 A | * | 7/1997 | Bryant | 606/62 |
| 5,908,423 A | * | 6/1999 | Kashuba et al. | 606/80 |
| 6,447,518 B1 | * | 9/2002 | Krause et al. | 606/80 |
| 6,467,557 B1 | * | 10/2002 | Krueger et al. | 175/45 |
| 7,407,440 B2 | | 8/2008 | White | |
| 2002/0094440 A1 | * | 7/2002 | Llanos et al. | 428/421 |
| 2002/0171208 A1 | | 11/2002 | Lechot et al. | |
| 2003/0176868 A1 | | 9/2003 | Pepper | |

(Continued)

FOREIGN PATENT DOCUMENTS

EP 0253526 A1 1/1988
WO WO-2006046789 A1 5/2006

(Continued)

*Primary Examiner* — Sunil K Singh
*Assistant Examiner* — Alan Snyder
(74) *Attorney, Agent, or Firm* — Blank Rome LLP; Peter S. Weissman

(57) ABSTRACT

Drive shaft for interchangeable reaming heads intended for surgical use, in particular a reaming head used prior to the positioning of an intramedullary nail in the femur or in a long bone. The shaft has a rod (20) made from composite material, e.g. carbon and/or glass fiber reinforced polymer, and a connection element (35) for the coupling of an interchangeable reaming head. One portion (32) of said connection element (35) is inserted into a cavity in the first end (21) of said rod (20). The inventive shaft has a constant diameter, a smooth external surface and a low cost such that it can be disposed of after use.

17 Claims, 4 Drawing Sheets

(56) References Cited

U.S. PATENT DOCUMENTS

2005/0043739 A1 2/2005 Sullivan et al.
2010/0144451 A1* 6/2010 Lawrie .......................... 464/80

FOREIGN PATENT DOCUMENTS

| WO | WO 2006046789 A1 * | 5/2006 |
| WO | WO-2009015672 A1 | 2/2009 |

* cited by examiner

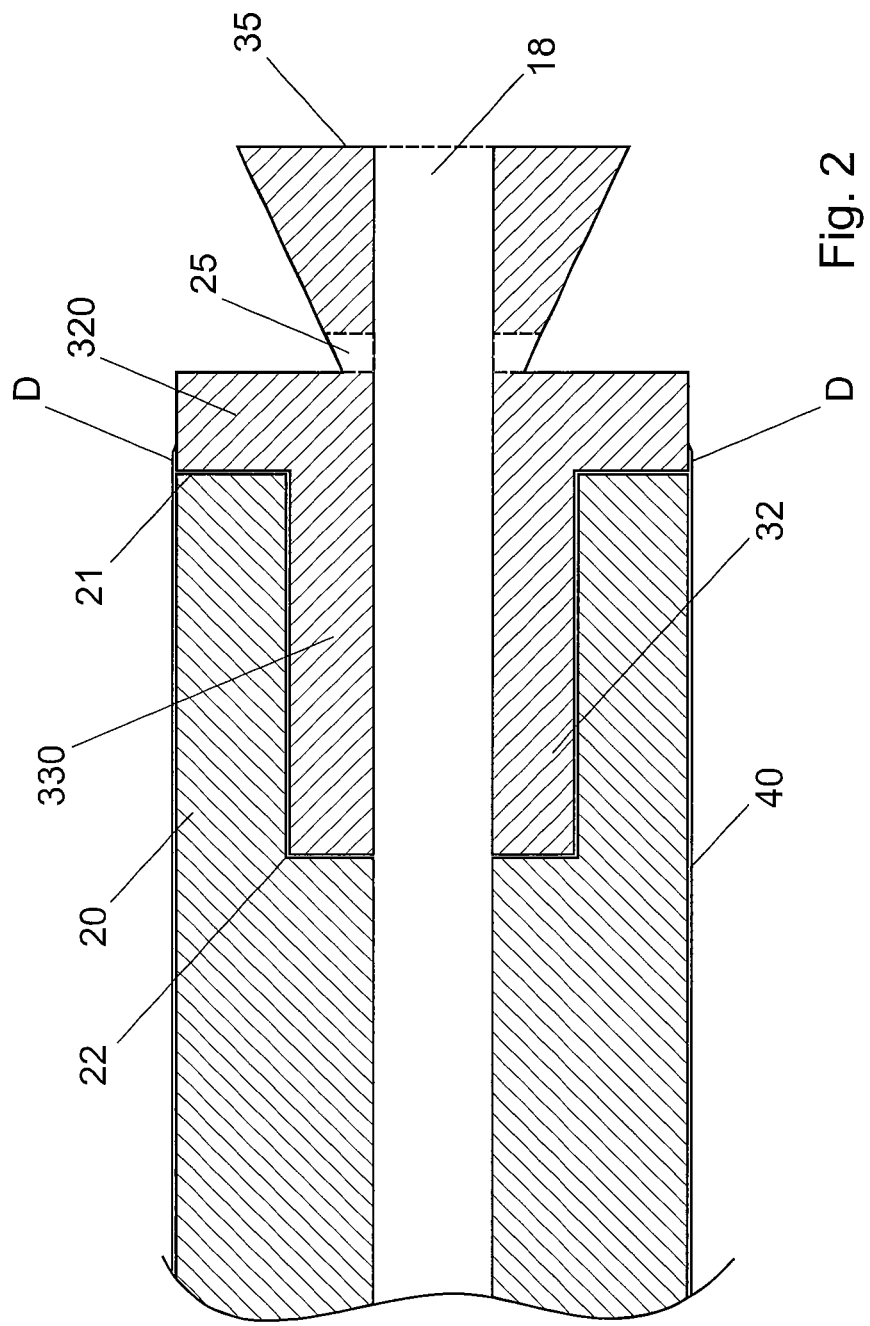

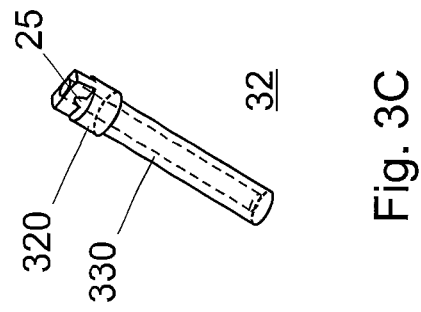
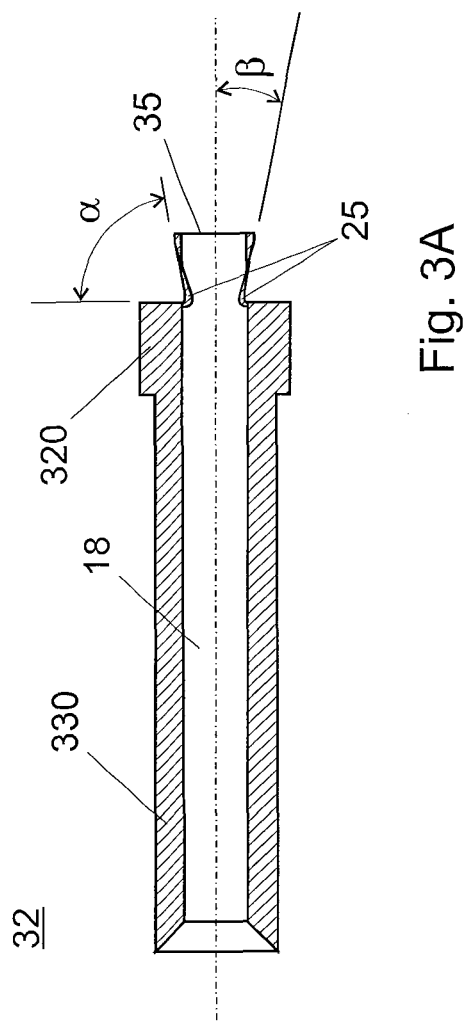
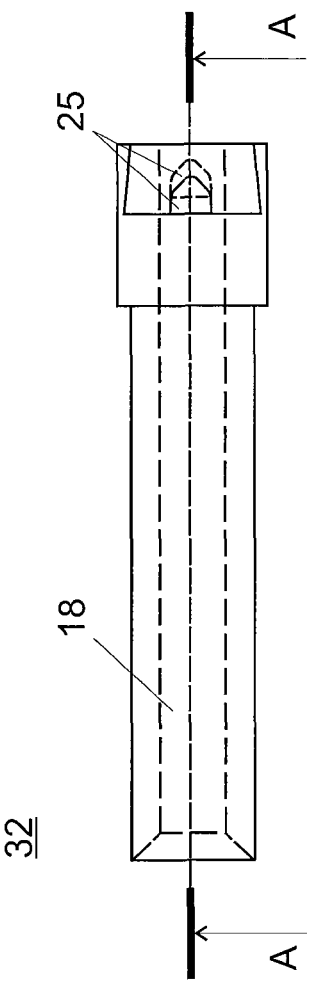

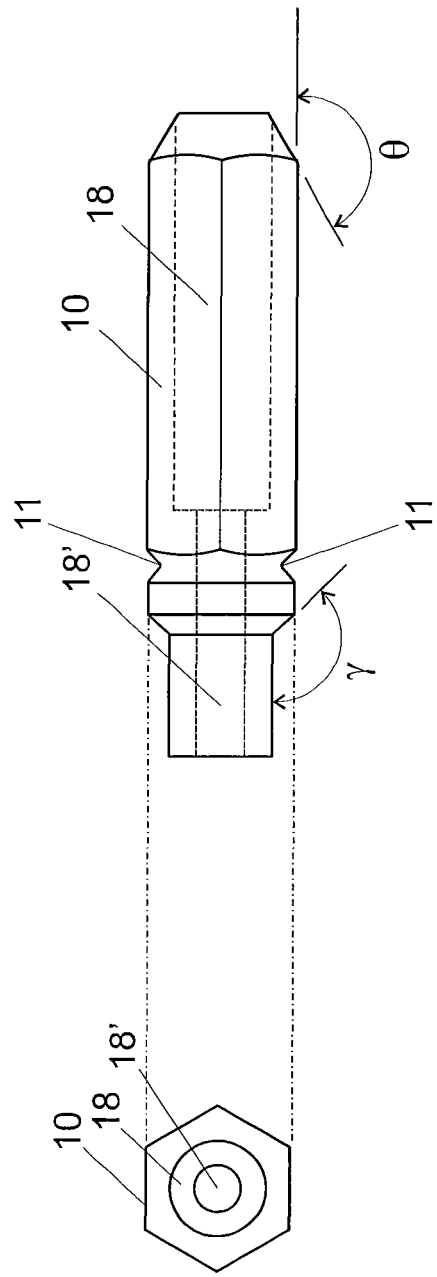

DRIVE SHAFT FOR A SURGICAL REAMER

This application is a continuation of PCT/EP2010/066120, filed Oct. 26, 2010, which claims priority to 2009CH-10657, filed Oct. 28, 2009, the entire contents of which are hereby incorporated by reference.

TECHNICAL FIELD

The present invention concerns a drive shaft for a surgical reamer, in particular a drive shaft with a structure made from composite material reinforced with long and/or short fibers, for driving an interchangeable reaming head for reaming or boring the intramedullary canal or cavity.

STATE OF THE ART

Centromedullary nailing is one of the most widely used therapeutic techniques in the treatment of fractures and in the reconstitution of long bones, for example and in a non limiting fashion the femur, but also the tibia or the humerus. According to this method, the medullary canal is widened to the desired diameter by means of several interchangeable reaming heads of different diameter mounted successively on a flexible drive shaft capable of following the curvature of the medullary canal.

Metallic drive shafts are known that have a helix structure that ensures the desire axial flexibility and rigidity to torsion. These devices are however costly and must be re-used. They are however difficult to clean and to sterilize, especially in a hospital environment.

U.S. Pat. No. 7,407,440 discloses tubular metallic shafts with a thin wall made of super-elastic materials, for example nitinol. Though these shafts are easier to clean and sterilize, they are however more costly and fragile than the conventional drive shafts.

WO2006/046789 describes a reamer in the field of industrial machines, for example for boring a hole in the camshaft of a vehicle engine, comprising a body composed by a first part of carbon fiber that is contained in a second metallic part, consisting of one or several parts. The second part protects the first one and affords the device better rigidity. An adapter inserted in the first part is designed to work, through a screw, with an interchangeable reaming head. A central metallic rod is inserted into the first part: its diameter is linked to the device's resonance frequency. Cooling liquid can circulate in the device when it is used at high speeds. The device of this application is not designed for reaming a bone, the aim being to increase the rigidity of the device and ream or bore holes at high speed without creating vibration effects.

WO2009/015672 relates to a transmission shaft made from carbon fiber and connection elements for the handle and the reamer. This device is not made of glass fiber and has a complicated distal coupling system.

BRIEF SUMMARY OF THE INVENTION

One aim of the present invention is to propose a drive shaft for reaming the medullary canal of long bones that is more economical and more reliable than the known devices.

Another aim is to propose a drive shaft for a surgical reamer that is easy and possible to sterilize in an industrial environment during its manufacture but that is sufficiently economical to be disposed of after the first use in order to avoid having to sterilize it in a hospital environment, which is more expensive.

Another aim of the present invention is to propose a drive shaft that is not as difficult to clean and sterilize as the devices of the prior art.

According to the invention, these aims are achieved notably by means of the device that is the object of the main claim, and notably by a drive shaft for a surgical reamer comprising a rod with a first extremity and a second extremity, a connection element for engaging an interchangeable reaming head, wherein the elongated rod has a composite structure comprising fibers, and wherein a portion of said connection element is inserted in a cavity of said first extremity of said rod.

This solution notably has the advantage that the drive shaft thus obtained is lighter and less expensive than the drive shafts of the prior art and can be used a single time and destroyed after use, thus avoiding the difficulties and the costs of sterilizing associated with the use of the known drive shafts.

This solution also makes it possible to achieve a flexible shaft with a metallic connection element at its extremity and a constant transverse section along the rod and the connection element, thus also making easier the insertion and withdrawal of the tool. This shaft is hollow to allow a Kirschner rod as reference to pass.

BRIEF DESCRIPTION OF THE FIGURES

Examples of embodiment of the invention are indicated in the description illustrated by the attached figures in which:

FIG. 2 shows in cross section one extremity of the transmission shaft of FIG. 1.

FIGS. 3a to 3c respectively show a cross-sectional view, a view from above and a side view of an embodiment of the invention.

FIGS. 4a to 4b respectively illustrate a cross-sectional and a lateral view of one extremity of an embodiment of the invention.

EXAMPLE(S) OF EMBODIMENTS OF THE INVENTION

Figure 1:
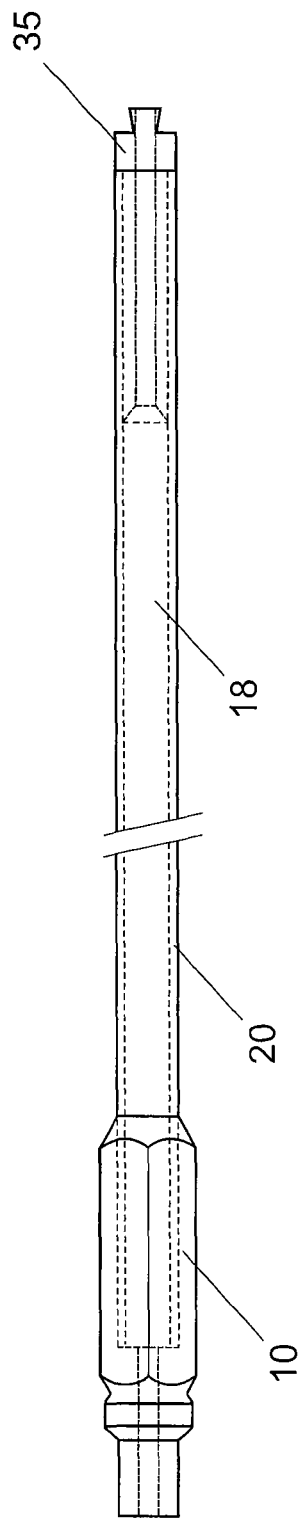
FIG. 1 illustrates an embodiment of the invention.

With reference to FIG. 1, according to one embodiment, the transmission shaft of the invention comprises a flexible rod 20 of composite material, for example with a fiber-reinforced plastic matrix. The length of the rod is adapted to that of the medullary canal of the bone on which one wishes to operate. In a preferred embodiment, this length is greater than 70 cm, for example 1 m, which advantageously makes it possible to perform arthrodesis in a single step. Known metallic transmission shafts with a wound coil have a length of approximately 50 cm and they thus do not allow arthrodesis to be performed in a single step. Furthermore, there are difficulties in making a known metallic transmission shaft with a length lower than 1 m, obtained by cutting a shaft of greater length, because of the spring's helix structure.

In a preferred embodiment, the inventive shaft is manufactured having a length of 1 m. As it is made of composite material, it is possible to cut it into two equal parts to have two shafts of 50 cm. Similarly, it is possible to cut it into two parts of unequal length and thus obtain two shafts with a different length. In other words, there are not two distinct manufacturing processes to make a shaft of 1 m length and a shaft of lesser length, for example 50 cm, since the shorter shaft is obtained from the shaft having a length of 1 m. To make a known metallic shaft with a length of 1 m, even without the aforementioned technical difficulties, would require a specific and thus costly production.

In the frame of the invention, different fibers can be used, depending on the mechanical and economic properties sought, for example glass fibers, carbon fibers or aramid fibers. The fibers are preferably embedded in a polymer matrix of epoxy resin, polyester, vinyl ester, phenolic ester, polyimide, polyamide, polypropylene, polyetheretherketone (PEEK) or any other appropriate material.

The tension and orientation of the fibers of the rod 20 are preferably predetermined and controlled so as to obtain a rod having the characteristics of flexibility in flexion and resistance to torsion required. According to one aspect of the invention, several superimposed layers of fibers are wound at tension on a cylindrical mandrel. The resin can be applied before or after winding. The orientation of the fibers relative to the axis of the rod and their tension are selected so as to achieve the desired mechanical characteristics. Conclusive tests have been carried out with a braiding comprising simultaneously fibers oriented at 45°, 90° and 135° relative to the shaft's longitudinal axis.

According to another aspect of the invention, the rod 20 is obtained from a web of long braided fibers (>10 cm) or of webbed ribbons, embedded in a matrix of the chosen resin and wound on a mandrel. The composite structure is thus achieved from pre-impregnated webs. In another variant, it is possible to inject such a shaft with a resin loaded with short glass or carbon fibers (<10 cm) to make shafts that have lower resistance to effort and have a low cost. In these cases too, the fibers have preferably predetermined orientations relative to the shaft's axis.

In a preferred embodiment, the rod 20 is provided with an element, such as a band or a thread or a powder that is radio-opaque, which enables it to be visualized radiographically during the operation.

The rod 20 comprises an interface element 10 at one extremity for connection to a motor, a drill or a handle, enabling the surgeon to guide and rotate the reaming head. In the example illustrated in FIGS. 1, 4a and 4b, the interface 10 has a standardized hexagonal section, visible notably in FIG. 4b. The value of the first angle γ and of the second angle θ in the variant of FIG. 4b are respectively 135° and 150°. Other structures are however possible.

The interface 10 has, as shown in detail in FIG. 4a, an axial channel 18 that traverses the drive shaft from one extremity to the other and also a channel 18', of a diameter smaller than the diameter of the channel 18, for insertion of the Kirschner rod. As illustrated in FIG. 4b, the coupling between the channel 18' and the channel 18 makes it more complicated to clean the device.

The groove 11 has a geometry adapted to each type of drill: FIG. 4b illustrates one example of such geometry.

The connection element 35 is connected to a first extremity of the rod 20 and enables interchangeable tools, for example a reaming head, a screw or any other orthopedic tool to be engaged. In the example illustrated in FIGS. 2 to 3c, the connection element 35 comprises a dovetail pin, designed to engage into a groove having a trapezoidal cross section of a reaming head. The dovetail pin is only one possible example of the connection element and other connection elements can be used.

In the event that the reaming head does not have a connection element, for example a dovetail, with a geometry that is compatible with that of the shaft's connection element 35, it is possible to use an intermediary mechanical coupling device to connect the reaming head to the shaft. This coupling device can be external and/or internal. External couplings can be for example of the type dovetail, sliding pivot, bayonet, T-shape, external extensible gripper etc. Internal couplings can be for example of the type internal extensible gripper, splined shaft, with a polygonal profile, with loose pins etc.

A transverse hole 25 enables the tool to be secured to the shaft by means of a pin or of a screw. Other fastening means are however possible. Nevertheless, the presence of a Kirschner rod is generally sufficient for securing the tool.

Because of the mechanical efforts and the delicate machining to which it must be subjected, the connection element 35 is preferably made of surgical stainless steel or of any other biocompatible metallic material. The connection element 35 comprises a portion 32 having a reduced transverse dimension, better visible in FIGS. 2 to 3c, inserted into a clearance at the first extremity of the composite rod 20. This portion 32 in one variant comprises a first part 320 having a diameter equal to the outer diameter of the rod 20 and a second part 330 having a reduced diameter similar to the diameter on the connection element 35. In the variant illustrated in FIG. 3a, the angle that defines the opening of the element 35 is equal to $2*\beta$. In the variant illustrated, $\beta=10°$. In the same figure, the angle between the element 35 and the part 320 of the portion 32 is indicated by the reference $\alpha$. In the illustrated variant, $\alpha=80°$.

The rod 20, the connection element 35 and the interface element 10 preferably have an axial channel 18 traversing the drive shaft from one extremity to the other. This characteristic enables the inventive shaft to be slid onto a Kirschner rod previously inserted into the medullary canal.

The transverse diameter of the connection element 35 is preferably equal to the outer transverse diameter of the rod 20, thus resulting in a drive shaft having a constant section, from its extremity up to the interface element 10, and whose external surface is perfectly smooth. This structure ensures that the insertion and withdrawal of the drive shaft are easy and minimizes the risk of blockage of the tool in the medullary cavity; it further makes sterilization easier. In any case, the device has not been designed for it to be sterilized. In another variant, for example illustrated in FIGS. 1 and 3a, the outer transverse diameter of the connection element 35 is less than the outer transverse diameter of the rod 20.

In one variant, the outer transverse diameter of the rod 20 is approximately 8 mm, for bones such as the femur. In another variant, this diameter is approximately 5-6 mm, for smaller bones such as the tibia or any other long bone. As discussed, the diameter of the connection element 35 has a diameter that adapts to that of the outer one of the rod 20.

In similar fashion, the inner diameter of the axial channel 18 through the connection element is equal to the inner diameter of the axial channel through the rod 20. This ensures a smooth channel surface, which makes it easier to insert the shaft around a pre-inserted guiding rod in the bone.

In a variant, not represented, the inner channel of the rod has a constant diameter and does not have a clearing for the connection element 35, which in this case forms a projection limiting the channel's inner diameter. This solution is less costly but makes the insertion of the reamer on the guiding rod slightly more difficult.

Several tests have shown that the coupling between the connection element 35 and the rod 20, and even the rod assembly, are sturdier if the latter is made of resin that is fiber reinforced resin rather than carbon fiber reinforced for example. A possible explanation for this unexpected phenomenon is that the rods made from carbon fiber or other high-performance fibers must have a very reduced wall thickness to offer the required flexibility in order to follow the curvature of the medullary cavity. A rod with a very thin wall from carbon fiber is indeed resistant in flexion but will however show poor resistance to crushing. Furthermore, the very thin walls that would be necessary in the case of manufacture from carbon fiber would not allow a connection element 35 with a diameter of the channel 18 equal to that of the axial channel in the rod to be inserted. Use of glass fiber is preferred.

The coupling between the connection element 35 and the elongated rod 20 can be improved by structuring the surface of the portion 32 with reduced transverse dimension and/or the internal surface of the cavity in which it is lodged, by ribbings, protuberances and cavities. The portion 32 with reduced transverse dimension is preferably held in its housing by an adhesive layer 22, for example a hot-melt adhesive, or an epoxy adhesive, or any other adhesive have excellent adhesion properties to the metal of the connection element 35 and the resin of the matrix of the rod 20. In one variant, this adhesive is a hot-melt glue, so that in the event that the shaft were to be brought to high temperatures, for example during a sterilization process, this glue would lose it mechanical properties and the shaft would be unusable. The presence of this glue, in other words, prevents the shaft from being used a second time, which is thus for one-way use. This adhesive is also present between the rod 20 and the interface element 10. The portion 32 with reduced dimension and its housing can possibly have a non-round cross section, for example a square section, in order to better transmit the rotation torque to the tool.

According to another aspect of the invention, the portion 32 with reduced transverse dimension is held in its housing by fastening means such as screws, rivets or tabs. These fastening means can be used singly or in combination with an adhesive as mentioned here above. The screw or rivet heads are preferably sheltered in countersinks, so as to not exceed beyond the smooth outer surface of the rod 20. According to another preferred embodiment of the invention, at least part of the rod 20 is covered with a biocompatible film 40. The internal surface of the channel 18 can also be covered in the same manner. As illustrated by the details D of FIG. 2, this film 40 also covers part of the portion 32 of the connection element so as to guarantee the tightness of the device.

The present invention enables flexible and resistant drive shafts to be made at a reduced manufacturing cost. These shafts can advantageously be used as one-way tools in operations for fitting centromedullary nails, thus avoiding all cleaning and sterilization problems of the known drive shafts.

REFERENCE NUMBERS USED IN THE FIGURES

10 Interface element
11 Groove of the interface element
20 Rod
18 Axial channel
18' Channel for insertion of the Kirschner rod
21 First extremity of the rod
22 Adhesive
25 Transverse hole
32 Portion of the connection element
320 First part of the portion of the connection element
330 Second part of the portion of the connection element
35 Connection element
40 Biocompatible film $\alpha$ Angle between the connection element 35 and the first part 320
$\beta$ Semi-opening of the connection element 35
$\gamma$ First angle of the interface element 10
$\theta$ Second angle of the interface element 10

The invention claimed is:

1. A drive shaft for a surgical reamer comprising a one-piece flexible elongated rod with a first extremity and a second extremity, a connection element configured to engage an interchangeable reaming head, wherein the elongated rod has a composite structure comprising fibers, wherein a portion of said connection element which is of reduced diameter is inserted in a cavity of the first extremity of said rod, and a widest part of the connection element is partly inside the rod.

2. The drive shaft of claim 1, having a transverse diameter that is essentially constant.

3. The drive shaft of claim 1, wherein said transverse diameter is comprised in the range 5-8 mm.

4. The drive of claim 1, wherein said composite structure comprises glass fibers.

5. The drive of claim 1, wherein said composite structure comprises wound fibers.

6. The drive of claim 1, wherein said composite structure is made from pre-impregnated webs.

7. The drive shaft of claim 1, wherein said rod is at least partly covered by a biocompatible film.

8. The drive shaft of claim 1, wherein said rod and said connection element have an axial channel.

9. The drive shaft of claim 8, wherein the diameter of said axial channel is essentially constant.

10. The drive shaft of claim 1, wherein said connection element comprises a dovetail pin designed to engage into a groove having a trapezoidal cross section of a reaming head and/or into an intermediary mechanical coupling device.

11. The drive shaft of claim 1, wherein said portion of the connection element inserted in a cavity of said rod is held by an adhesive.

12. The drive shaft of claim 11, wherein said adhesive is hot-melt glue.

13. The drive shaft of claim 1, wherein said portion of the connection element inserted in a cavity of said rod is held by fastening means.

14. The drive shaft of claim 1, wherein the second extremity of said rod bears an interface element that can be connected with a drill or with a handle.

15. The drive shaft of claim 1, comprising a radio-opaque element.

16. The drive shaft of claim 1, having a length greater than 70 cm.

17. A drive shaft for a surgical reamer comprising a one-piece flexible elongated rod with a first extremity and a second extremity, a connection element configured to engage an interchangeable reaming head, wherein the elongated rod has a composite structure comprising fibers, wherein a portion of said connection element which is of reduced diameter is inserted in a cavity of the first extremity of said rod, wherein said composite structure comprises glass fibers oriented at 45°, 90° and 135° relative to an original axis, and a widest part of the connection element is partly inside the rod.

* * * * *